United States Patent [19]

MacCoss et al.

[11] Patent Number: 5,728,716
[45] Date of Patent: Mar. 17, 1998

[54] ARALKYLAMINO SUBSTITUTED AZACYCLIC THERAPEUTIC AGENTS

[75] Inventors: Malcolm MacCoss, Freehold, N.J.; Christopher John Swain, Duxford, United Kingdom

[73] Assignee: Merck Sharp & Dohme Limited, Hoddesdon, England

[21] Appl. No.: 676,156

[22] PCT Filed: Jan. 26, 1995

[86] PCT No.: PCT/GB95/00153

§ 371 Date: Jul. 11, 1996

§ 102(e) Date: Jul. 11, 1996

[87] PCT Pub. No.: WO95/20575

PCT Pub. Date: Aug. 3, 1995

[30] Foreign Application Priority Data

Jan. 28, 1994 [GB] United Kingdom ............. 9401639
Jan. 28, 1994 [GB] United Kingdom ............. 9401642

[51] Int. Cl.⁶ .................................... A01N 43/40
[52] U.S. Cl. .................. 514/326; 514/329; 546/210; 546/223
[58] Field of Search .................... 514/326, 329; 546/210, 223

[56] References Cited

FOREIGN PATENT DOCUMENTS

| A 0 436 334 | 7/1991 | European Pat. Off. |
| WO 91/09844 | 7/1991 | WIPO . |
| WO A 93 01170 | 1/1993 | WIPO . |
| WO A 93 21181 | 10/1993 | WIPO . |
| WO A 94 03445 | 2/1994 | WIPO . |

OTHER PUBLICATIONS

*Chemical Abstracts*, vol. 120, No. 5, Jan. 31, 1994, abstract No. 45616t, p. 74.

Tattersall, et al, *Eur. J. Pharmacol.*, vol. 250, No. 1, 1993, pp. r5–r6, "The tachykinin NK1 receptor antagonist CP–99994 attenuates cisplatin induced emesis in the ferret".

*Primary Examiner*—C. Warren Ivy
*Assistant Examiner*—Garth M. Dahlen
*Attorney, Agent, or Firm*—J. Eric Thies; David L. Rose

[57] ABSTRACT

Aralkylamino substituted azacyclic compounds of formula (I) and their salts and prodrugs. The variables are defined herein. The compounds are useful as tachykinin antagonists and are of particular use in the treatment of pain, inflammation, migraine, and emesis.

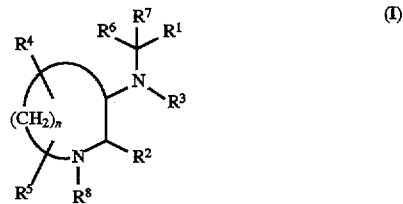

13 Claims, No Drawings

ARALKYLAMINO SUBSTITUTED AZACYCLIC THERAPEUTIC AGENTS

This application is a 371 of PCT/GB95/00153, Jan. 26, 1995.

This invention relates to a class of azacyclic compounds, which are useful as tachykinin antagonists. More particularly, the compounds of the invention comprise an azacyclic ring system substituted by an aralkylamino moiety.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in *"Trends in Cluster Headache"* Ed. Sicuteri et al Elsevier Scientific Publishers, Amsterdam (1987) page 85)] and emesis [F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet*, 11 Nov. 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol.*

*Physiol.* (1988) 66, 1361-7], immunoregulation [Lotz et al, *Science* (1988) 241, 1218-21 and Kimball et al, *J. Immunol.* (1988) 141(10), 3564-9] vasodilation, bronchospasm, reflex or neuronal control of the viscera [Mantyh et al, *PNAS* (1988) 85, 3235-9] and, possibly by arresting or slowing β-amyloid-mediated neurodegenerative changes [Yankner et al, *Science* (1990) 250, 279-82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554-7].

Substance P may also play a role in demyelinating diseases such as multiple sclerosis and amyotrophic lateral sclerosis [J. Luber-Narod et al, poster *C.I.N.P. XVIIIth Congress*, 28th Jun.-2nd Jul. 1992], and in disorders of bladder function such as bladder detrusor hyper-reflexia (*Lancet*, 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists. By virtue of their non-peptide nature, the compounds of the present invention do not suffer from the shortcomings, in terms of metabolic instability, of the known peptide-based tachykinin antagonists discussed above.

The present invention provides a compound of formula (I), or a pharmaceutically acceptable salt or prodrug thereof:

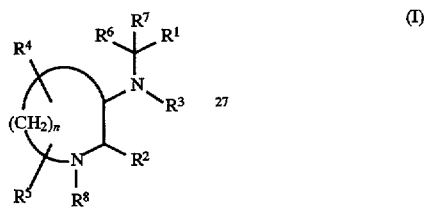

wherein n is 1, 2 or 3 and where any carbon atom of $(CH_2)_n$ may be substituted by $R^4$ and/or R5;

$R^1$ represents $(CH_2)_q$phenyl, wherein q is zero, 1, 2 or 3, which may be optionally substituted in the phenyl ring by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, $-OR^a$, $-SR^a$, $-SOR^a$, $-SO_2R^a$, $-NR^aR^b$, $-NR^aCOR^b$, $-NR^aCO_2R^b$, $-COR^a$, $-CO_2R^a$ and $-CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^3$ represents H or $C_{1-6}$alkyl;

$R^4$ and $R^5$ each independently represent H, halo, $C_{1-6}$alkyl, oxo, $CO_2R^a$ or $CONR^aR^b$;

$R^6$ represents H or $C_{1-6}$alkyl;

$R^7$ represents H, $C_{1-6}$alkyl optionally substituted by a hydroxy group, or $(CH_2)_pNR^9R^{10}$, $CO_2R^{16}$, $CONR^9R^{10}$, $(CH_2)_pCO_2R^{16}$, $(CH_2)_pCONR^9R_{10}$, $(CH_2)_pNR^9COR^{16}$, $(CH_2)_pNHSO_2R^{11}$, $(CH_2)_pOR^{16}$, $(CH_2)_pOC(O)R^9$, $(CH_2)_pOC_{1-4}$alkylCOR$^{17}$, or phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ and —$CONR^aR^b$;

$R^8$ represents H, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, cyano, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}alkylR^{12}$, $CONR^{13}C_{2-6}$alkynyl, $CONR^{13}C_{2-6}$alkenyl, $COCONR^aR^b$, $CONR^aC(NR^b)NR^aR^b$, $CONR^a$heteroaryl, and phenyl optionally substituted by one or more substituents selected from $C_{1-6}$alkyl, $C_{1-6}$alkoxy, halo and trifluoromethyl) or $C_{1-6}$alkyl, optionally substituted by oxo, substituted by an optionally substituted aromatic heterocycle;

with the proviso that when $R^6$ and $R^7$ both represent H, $R^8$ represents $C_{1-6}$alkyl optionally substituted by oxo, substituted by an optionally substituted aromatic heterocycle selected from pyrrolyl, pyrazolyl, pyrazinyl, pyridazinyl, oxadiazolyl, thiadiazolyl, imidazolyl, benzimidazolyl, benzoxazolyl, benzthiophenyl, benzofuranyl and indolyl, or a substituted aromatic heterocycle selected from thienyl, furyl, pyridyl, triazolyl, tetrazolyl, thiazolyl, oxazolyl, quinolyl, isoxazolyl and isothiazolyl;

$R^a$ and $R^b$ each independently represent H, $C_{1-6}$alkyl, trifluoromethyl or phenyl optionally substituted by $C_{1-6}$alkyl, halo or trifluoromethyl;

$R^9$ and $R^{10}$ each independently represent H or $C_{1-6}$alkyl;

$R^{11}$ represents $NR^{14}R^{15}$ or an optionally substituted aromatic or non-aromatic azacyclic or azabicyclic group;

$R^{12}$ represents $OR^a$, $CONR^aR^b$ or heteroaryl;

$R^{13}$ represents H or $C_{1-6}$alkyl;

$R^{14}$ and $R^{15}$ each independently represent H, $C_{1-6}$alkyl, phenyl optionally substituted by one or more of $C_{1-6}$alkyl, $C_{1-6}$alkoxy, halo or trifluoromethyl, or phenyl$C_{1-4}$alkyl optionally substituted in the phenyl ring by one or more of $C_{1-6}$alkyl, $C_{1-6}$alkoxy, halo or trifluoromethyl;

$R^{16}$ represents $C_{1-6}$alkyl;

$R^{17}$ represents $C_{1-6}$alkoxy, amino, $C_{1-4}$alkylamino or di($C_{1-4}$alkyl)amino; and p is 1 to 4.

As used herein, the definition of each expression, when it occurs more than once in any structure, is intended to be independent of its definition elsewhere in the same structure.

The alkyl, alkenyl and alkynyl groups referred to with respect to the above formula may represent straight, branched or cyclic groups. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. In particular, the relative orientation of the 2- and 3- substituents on the azacyclic ring may give rise to cis and trans diastereoisomers, of which the cis stereochemistry is preferred. It is to be understood that all such isomers and mixtures thereof are encompassed within the scope of the present invention.

Preferably n is 2 or 3, more preferably 3.

Preferably q is zero and $R^1$ represents substituted phenyl. When $R^1$ is substituted phenyl suitable substituents include nitro, trifluoromethyl, trimethylsilyl, bromo, chloro, fluoro, iodo, cyano, methyl, ethyl, cyclopropyl, vinyl, methoxy, phenoxy, amino and carbonylmethoxy. Preferably $R^1$ represents phenyl substituted by one or more groups selected from methyl, trifluoromethyl, chloro and t-butyl.

Preferably $R^1$ represents disubstituted phenyl, more preferably 3,5-disubstituted phenyl such as 3,5-dichlorophenyl or 3,5-bis(trifluoromethyl)phenyl, or monosubstituted phenyl, such as 3-substituted phenyl, e.g. 3-t-butylphenyl.

Preferably $R^2$ represents unsubstituted benzhydryl, phenyl substituted by halo such as fluoro, for example 4-fluorophenyl, or unsubstituted phenyl, more preferably unsubstituted phenyl.

Preferably $R^4$ and $R^5$ both represent H.

Suitable values for $R^6$ include H, methyl and ethyl. Preferably $R^6$ represents H or methyl, more preferably H.

Preferably $R^7$ represents $C_{1-6}$alkyl optionally substituted by a hydroxy group, such as methyl, ethyl, $CH_2OH$, $CH_2CH_2OH$, $CH(OH)CH_3$ or $C(OH)(CH_3)_2$, more preferably methyl or $CH_2OH$.

When $R^8$ represents $C_{1-6}$alkyl, optionally substituted by oxo, substituted by a substituted aromatic heterocycle, suitable substituents in the heterocyclic ring include $C_{1-6}$alkyl, $C_{1-6}$alkoxy, oxo, thioxo, halo, trifluoromethyl, $NR^aR^b$, $NR^aCOR^b$, $CONR^aR^b$, $CO_2R^a$, $SO_2R^a$ and $CH_2OR^a$, where $R^a$ and $R^b$ are as previously defined.

Preferably $R^8$ represents $C_{1-3}$alkyl such as methyl, ethyl or i-propyl substituted by a substituted or unsubstituted aromatic heterocycle. Suitable heterocycles include thienyl, furyl, pyrrolyl, pyridyl, pyrazolyl, triazolyl, tetrazolyl, thiazolyl, pyrazinyl, pyridazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl.

In one group of compounds according to the invention $R^8$ represents $CH_2$-Het, $CH(CH_3)$-Het, $C(CH_3)_2$-Het or $C(O)$-Het, where Het is pyrrolyl, pyrazolyl, pyrazinyl, pyridazinyl, oxadiazolyl, thiadiazolyl, imidazolyl, benzimidazolyl, benzoxazolyl, benzothiophenyl, benzofuranyl or indolyl.

Preferably $R^8$ represents $CH_2$-Het, $CH(CH_3)$-Het, $C(CH_3)_2$-Het or $C(O)$-Het where Het is substituted or unsubstituted oxazolyl, oxadiazolyl, tetrazolyl, thiazolyl, thiadiazolyl, furanyl, thienyl, triazolyl, pyrazinyl, pyridyl, pyridazinyl, imidazolyl or benzimidazolyl. More preferably Het is triazolyl or triazolyl substituted by oxo.

Other suitable values for $R^8$ include H, $COR^a$, $CO_2R^a$, $COCONR^aR^b$, $COCO_2R^a$, $C_{1-6}$alkyl and $C_{1-6}$alkyl substituted by a group selected from $CO_2R^a$, $CONR^aR^b$, CN, C(NOH)NR$^a$R$^b$, CONHphenyl(C$_{1-4}$alkyl), optionally substituted phenyl, CONHNR$^a$R$^b$, COCONR$^a$R$^b$, CONR$^a$C(NH)NH$_2$, CSNR$^a$R$^b$, CONR$^{13}$C$_{2-6}$alkynyl, CONR$^a$C$_{1-6}$alkylR$^{12}$ and CONR$^a$heteroaryl.

It will be appreciated that, when R$^8$ comprises a heteroaryl moiety substituted by an oxo or thioxo substituent, different tautomeric forms are possible so that the substituent on the heteroaryl moiety may be represented as =O or —OH, or =S or —SH, respectively. For the avoidance of doubt, all such tautomeric forms are embraced by the present invention.

When R$^{11}$ represents NR$^{14}$R$^{15}$, R$^{14}$ and R$^{15}$ are preferably both C$_{1-6}$alkyl such as methyl, ethyl, n-propyl, i-propyl, n-butyl, i-butyl or t-butyl. More preferably R$^{14}$ and R$^{15}$ will both represent methyl.

When R$^{11}$ represents an aromatic or non-aromatic azacycle or azabicycle it may contain one or more additional heteroatoms selected from O, S and N or groups NR$^{18}$, where R$^{18}$ is H, C$_{1-6}$alkyl or phenylC$_{1-4}$alkyl, and may be unsubstituted or substituted. Suitable substituents include C$_{1-6}$alkyl, C$_{1-6}$alkoxy, oxo, SH, =S, halo, trifluoromethyl, NR$^a$R$^b$, NR$^a$COR$^b$, CONR$^a$R$^b$, CO$_2$R$^a$ and CH$_2$OR$^a$, where R$^a$ and R$^b$ are as previously defined.

When R$^{11}$ represents an aromatic azacycle or azabicycle, suitable values of R$^{11}$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When R$^{11}$ represents a non-aromatic azacycle or azabicycle, suitable values of R$^{11}$ include morpholinyl, piperdinyl, pyrrolidinyl, piperazinyl, methylpiperazinyl, azanorbornanyl, azabicyclo[2.2.2]octanyl and azabicyclo[3.2.2]nonyl, preferably morpholinyl, pyrrolidinyl, methylpiperazinyl, quinuclidinyl (azabicyclo[2.2.2]octanyl) or azabicyclo[3.2.2]nonyl, more preferably pyrrolidinyl.

A particular sub-class of compounds according to the present invention is represented by compounds of formula (Ia), and pharmaceutically acceptable salts and prodrugs thereof:

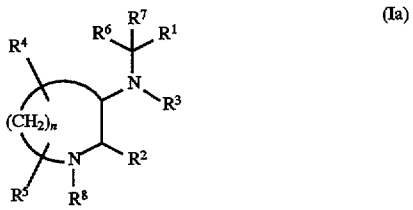

wherein

R$^1$, R$^2$, R$^3$, R$^4$, R$^5$, R$^6$, R$^8$ and n are as defined for formula (I) above; and R$^7$ represents C$_{1-6}$alkyl optionally substituted by a hydroxy group, or (CH$_2$)$_p$NR$^9$R$^{10}$, CO$_2$R$^{16}$, CONR$^9$R$^{10}$, (CH$_2$)$_p$CO$_2$R$^{16}$, (CH$_2$)$_p$CONR$^9$R$^{10}$, (CH$_2$)$_p$NR$^9$COR$^{16}$, (CH$_2$)$_p$NHSO$_2$R$^{11}$, (CH$_2$)$_p$OR$^{16}$, (CH$_2$)$_p$OC(O)R$^9$, (CH$_2$)$_p$OC$_{1-4}$alkylCOR$^{17}$, or phenyl optionally substituted by 1, 2 or 3 groups selected from C$_{1-6}$alkyl, C$_{2-6}$alkenyl, C$_{2-6}$alkynyl, halo, cyano, nitro, trifluoromethyl, trimethylsilyl, —OR$^a$, —SR$^a$, —SOR$^a$, —SO$_2$R$^a$, —NR$^a$R$^b$, —NR$^a$COR$^b$, —NR$^a$CO$_2$R$^b$, —COR$^a$, —CO$_2$R$^a$ and —CONR$^a$R$^b$.

A preferred sub-class of compounds according to the present invention is represented by compounds of formula (Ib), and pharmaceutically acceptable salts and prodrugs thereof:

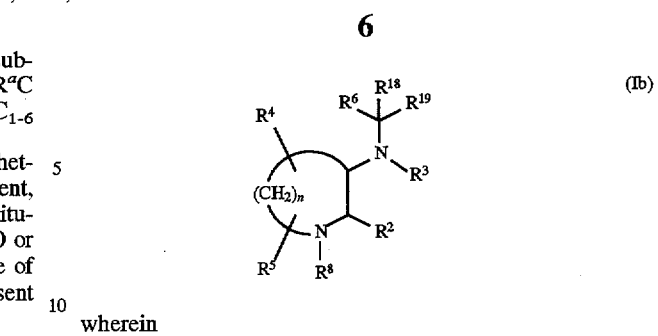

wherein

R$^2$, R$^3$, R$^4$, R$^5$, R$^6$, R$^8$ and n are as defined for formula (I) above;

R$^{18}$ represents C$_{1-6}$alkyl optionally substituted by a hydroxy group; and R$^{19}$ represents phenyl optionally substituted by 1, 2 or 3 groups selected from C$_{1-6}$alkyl, C$_{2-6}$alkenyl, C$_{2-6}$alkynyl, halo, cyano, nitro, trifluoromethyl, trimethylsilyl, —OR$^a$, —SR$^a$, —SOR$^a$, —SO$_2$R$^a$, —NR$^a$R$^b$, —NR$^a$COR$^b$, —NR$^a$CO$_2$R$^b$, —COR$^a$, —CO$_2$R$^a$ and —CONR$^a$R$^b$.

A further preferred sub-class of compounds according to the present invention is represented by compounds of formula (Ic) and pharmaceutically acceptable salts and prodrugs thereof:

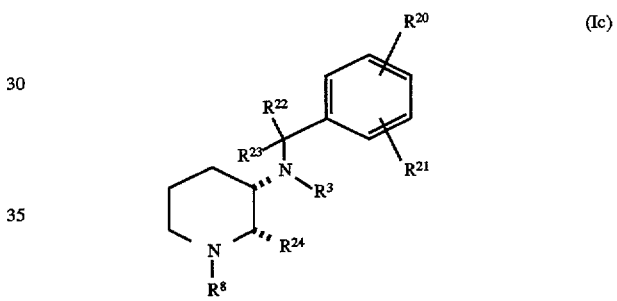

wherein

R$^3$ and R$^8$ are as defined for formula (I);

R$^{20}$ and R$^{21}$ independently represent H, C$_{1-6}$alkyl, C$_{2-6}$alkenyl, C$_{2-6}$alkynyl, chloro, bromo, fluoro, iodo, cyano, nitro, trifluoromethyl, trimethylsilyl, OR$^a$, SR$^a$, SOR$^a$, SO$_2$R$^a$, NR$^a$R$^b$, NR$^a$COR$^b$, NR$^a$CO$_2$R$^b$, COR$^a$, CO$_2$R$^a$ or CONR$^a$R$^b$, where R$^a$ and R$^b$ are as previously defined;

R$^{22}$ is methyl optionally substituted by hydroxy;

R$^{23}$ is H or methyl; and

R$^{24}$ represents phenyl or benzhydryl wherein any of the phenyl rings of the phenyl or benzhydryl moieties may optionally be substituted by halo or trifluoromethyl, preferably unsubstituted phenyl.

Particular values of R$^{20}$ and R$^{21}$ include methyl, ethyl, t-butyl, chloro, fluoro and trifluoromethyl. Preferably R$^{20}$ and R$^{21}$ are both other than hydrogen and are located at the 3- and 5-positions of the phenyl ring.

A preferred group of compounds according to the present invention are compounds of formula (Ic) wherein R$^8$ is optionally substituted triazolyl.

Another particular sub-class of compounds according to the present invention is represented by compounds of formula (Id), and pharmaceutically acceptable salts and prodrugs thereof:

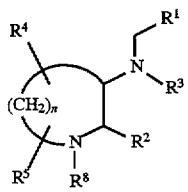

(Id)

wherein

R¹, R², R³, R⁴, R⁵, and n are as defined for formula (I) above; and

R⁸ represents $C_{1-6}$alkyl, optionally substituted by oxo, substituted by an optionally substituted aromatic heterocycle selected from pyrrolyl, pyrazolyl, pyrazinyl, pyridazinyl, oxadiazolyl, thiadiazolyl, imidazolyl, benzimidazolyl, benzoxazolyl, benzthiophenyl, benzofuranyl and indolyl, or a substituted aromatic heterocycle selected from thienyl, furyl, pyridyl, triazolyl, tetrazolyl, thiazolyl, oxazolyl, quinolyl, isoxazolyl and isothiazolyl.

Another particularly preferred sub-class of compounds according to the present invention is represented by compounds of formula (Ie), and pharmaceutically acceptable salts and prodrugs thereof:

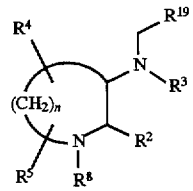

(Ie)

wherein R², R³, R⁴, R⁵, R⁸ and n are as defined for formula (Id) above; and

R¹⁹ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —OR$^a$, —SR$^a$, —SOR$^a$, —SO₂R$^a$, —NR$^a$R$^b$, —NR$^a$COR$^b$, —NR$^a$CO₂R$^b$, —COR$^a$, —CO₂R$^a$ and —CONR$^a$R$^b$.

A yet further preferred sub-class of compounds according to the present invention is represented by compounds of formula (If) and pharmaceutically acceptable salts and prodrugs thereof:

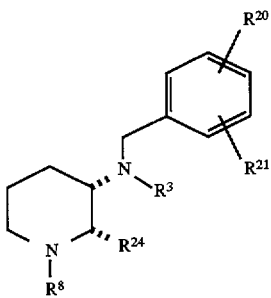

(If)

wherein

R³ and R⁸ are as defined for formula (I);

R²⁰ and R²¹ independently represent H, $C_{1-6}$alkyl, $C_{2-6}$alkenyl, $C_{2-6}$alkynyl, chloro, bromo, fluoro, iodo, cyano, nitro, trifluoromethyl, trimethylsilyl, OR$^a$, SR$^a$, SOR$^a$, SO₂R$^a$, NR$^a$R$^b$, NR$^a$COR$^b$, NR$^a$CO₂R$^b$, COR$^a$, CO₂R$^a$ or CONR$^a$R$^b$, where R$^a$ and R$^b$ are as previously defined; and R²⁴ represents phenyl or benzhydryl wherein any of the phenyl rings of the phenyl or benzhydryl moieties may optionally be substituted by halo or trifluoromethyl, preferably unsubstituted phenyl.

Particular values of R²⁰ and R²¹ include methyl, ethyl, t-butyl, chloro, fluoro and trifluoromethyl. Preferably R²⁰ and R²¹ are both other than hydrogen and are located at the 3- and 5-positions of the phenyl ring.

A preferred group of compounds according to the invention are compounds of formula (If) wherein R⁸ is substituted triazolyl.

Specific compounds within the scope of the present invention include:

cis-3-((3,5-bis(trifluoromethyl))(α-methyl)benzylamino)-2-(4-fluorophenyl) piperidine;

cis-[3-((3,5-bis(trifluoromethyl))benzylamino)-2-(4-fluorophenyl)piperidine-1-ylmethyl]-2,4-dihydro-[1,2,4]-triazol-3-one;

and pharmaceutically acceptable salts and prodrugs thereof.

For use in medicine, the salts of the compounds of formula (I) will be pharmaceutically acceptable salts. Other salts (such as the dibenzoyltartrate salts) may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising a compound of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former.

The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders and diseases of the GI tract such as disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, motion, surgery, migraine, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984)68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide. Additionally, a compound of formula (I) may be administered in combination with an anti-inflammatory corticosteroid, such as dexamethasone. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 2 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The compounds according to the present invention may be prepared by a process (A) which comprises reacting a compound of formula (II) with a compound of formula (III):

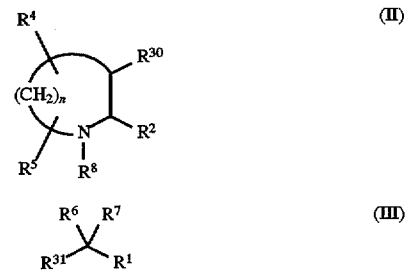

wherein $R^1$, $R^2$, $R^4$, $R^5$, $R^6$, $R^7$, $R^8$ and n are as defined for formula (I), except that any reactive moiety is protected by a suitable protecting group; and one of $R^{30}$ and $R^{31}$ represents a leaving group and the other of $R^{30}$ and $R^{31}$ represents $NHR^3$, where $R^3$ is as defined for formula (I); in the presence of a base, followed by deprotection, if required.

Suitably $R^{30}$ represents $NHR^3$ and $R^{31}$ represents a leaving group.

Suitable leaving groups include halo, e.g. chloro, bromo or iodo, or sulphonate derivatives such as tosylate, mesylate or triflate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, sodium hydride is used.

According to another process (B), compounds of formula (I) wherein $R^6$ is hydrogen, may be prepared by the reductive amination of a compound of formula (II) in which $R^{30}$ is the group $NHR^3$, with a compound of formula $R^1COR^7$, in the presence of a reducing agent. Suitable reducing agents for use in this reaction include, for example, sodium cyanoborohydride or sodium triacetoxyborohydride, or catalytic hydrogenation. The reaction is conveniently effected in a suitable solvent such as acetic acid or methanol at a temperature between 0° C. and 50° C., conveniently at about room temperature.

Alternatively, according to a further process (C), compounds of formula (I) may be prepared from different compounds of formula (I) by interconversion processes. In particular, interconversion processes may be used to vary the group $R^8$. For example, compounds of formula (I) wherein $R^8$ is other than H may be prepared from the corresponding compounds of formula (I) wherein $R^8$ is H by reaction with a reagent suitable to introduce the group $R^8$, for example, a halide or acyl halide, or corresponding mesylate or tosylate, of formula $R^8$-L, where L represents halo, such as chloro, bromo or iodo, methylsulphonate or p-toluenesulphonate, or any other suitable leaving group, in the presence of a base. Suitable bases of use in the reaction include inorganic bases such as alkali metal carbonates, for example, potassium carbonate. Conveniently the reaction is effected in a suitable organic solvent, for example, dimethylformamide.

Compounds of formula (I) wherein $R^8$ is $COR^a$ may be prepared from compounds of formula (I) wherein $R^8$ is H by, for example, reaction with an appropriate acid anhydride.

Compounds of formula (I) wherein $R^8$ is $C_{1-6}$alkyl may be prepared from corresponding compounds of formula (I) wherein $R^8$ is $COR^a$ by reduction using, for example, borane or a borohydride such as sodium cyanoborohydride.

Compounds of formula (I) wherein $R^8$ is $C_{1-6}$alkyl substituted by $CONR^aR^b$ may be prepared from corresponding compounds of formula (I) wherein $R^8$ is $C_{1-6}$alkyl substituted by $CO_2R^a$ by treatment with ammonia or an amine of formula $NR^aR^b$.

Compounds of formula (I) wherein $R^8$ is $C_{1-6}$alkyl substituted by 5-oxadiazolyl may be prepared from compounds of formula (I) wherein $R^8$ is $C_{1-6}$alkyl substituted by $CO_2R^a$, where $R^a$ represents $C_{1-6}$alkyl, by reaction with a compound of formula (IV)

wherein $R^{32}$ represents H or a suitable substituent, in the presence of a base.

Suitable bases of use in the reaction include alkali metals, such as, for example, sodium, and alkali metal hydrides, such as, for example, sodium hydride.

The reaction is conveniently effected in a suitable organic solvent. Which solvents will be appropriate will depend on the nature of the base used. For example, where the base used is an alkali metal, suitable solvents will include alcohols, for example, ethanol, whereas where the base used is an alkali hydride, suitable solvents will include ethers, for example, tetrahydrofuran.

Preferably the reaction is conducted at elevated temperature, such as the reflux temperature of the chosen solvent.

Compounds of formula (I) wherein $R^8$ is $C_{1-6}$alkyl substituted by tetrazolyl may be prepared from compounds of formula (I) wherein $R^8$ is $C_{1-6}$alkyl substituted by cyano by treatment with an alkali metal azide, such as sodium azide.

Compounds of formula (I) wherein $R^8$ is $C_{1-6}$alkyl substituted by thiazolyl may be prepared from compounds of formula (I) wherein $R^8$ is $C_{1-6}$alkyl substituted by $CSNH_2$ by reaction with a compound of formula Hal-$CH_2C(O)$—$R^{60}$, where Hal is halo, such as bromo, chloro or iodo, and $R^{60}$ represents H or a suitable substituent.

Compounds of formula (I) wherein $R^8$ is $C_{1-6}$alkyl substituted by thioxotriazolyl may be prepared from compounds of formula (I) wherein $R^8$ is $C_{1-6}$alkyl substituted by $CONHNH_2$ by reaction with a compound of formula $R^{61}NCS$, wherein $R^{61}$ represents H or a suitable substituent such as $C_{1-6}$alkyl, in the presence of a base.

Suitable bases of use in the reaction include organic bases such as, for example, 1,8-diazabicyclo[5.4.0]undec-7-ene (DBU). The reaction is conveniently effected in a suitable organic solvent, such as alcohol, e.g. butanol.

Compounds of formula (I) wherein $R^8$ is $C_{1-6}$alkyl substituted by unsubstituted or substituted triazolyl may be prepared from compounds of formula (V)

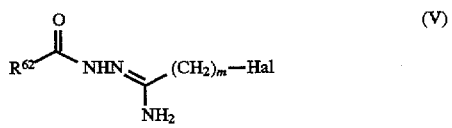

wherein Hal is as previously defined, m is 1, 2, 3, 4, 5 or 6 and $R^{62}$ is H or a group suitable as a substituent of the triazole ring, or convertable to such a group under the reaction conditions, in the presence of a base.

Suitable bases of use in the reaction include alkali metal carbonates, such as, for example, potassium carbonate.

Suitably $R^{62}$ represents H, $OCH_3$ (which is converted to an oxo substituent under the reaction conditions) or $CONH_2$.

The reaction is conveniently effected in an anhydrous organic solvent, such as, for example, anhydrous dimethylformamide, preferably at elevated temperature, such as about 60° C.

Compounds of formula (I) wherein $R^8$ represents $C_{1-6}$alkyl substituted by $CONR^aC_{1-6}$alkyl$R^{12}$ or $CONR^a$heteroaryl may be prepared from compounds of formula (I) wherein $R^8$ is $C_{1-6}$alkyl substituted by $CO_2H$ by reaction with an amine of formula $HNR^aC_{1-6}$alkyl$R^{12}$ or $HNR^a$heteroaryl.

Alternatively, compounds of formula (I) in which $R^7$ represents, in particular, $CO_2R^{16}$ may be converted into other compounds of formula (I). Thus compounds of formula (I) where $R^7$ is $CO_2R^{16}$ may be reacted with a Grignard reagent of formula $R^cMgHal$ where $R^c$ is an alkyl group and Hal is as previously defined to give compounds where $R^7$ is a tertiary alcohol. Secondary alcohols may be prepared firstly by reduction of the ester moiety to an aldehyde using, for example, diisobutylaluminium hydride, followed by reaction with either $R^cLi$ or $R^cMgHal$.

The aldehyde may also be used as a precursor for alkenyl intermediates where the group at position $R^7$ has the formula —CH=$CHR^d$, where $R^d$ is $(CH_2)_sNR^9R^{10}$, $(CH_2)_sCO_2R^{16}$, $(CH_2)_sCONR^9R^{10}$ or $(CH_2)_sNR^9COR^{16}$ (where s is 0, 1 or 2 and $R^9$, $R^{10}$ and $R^{16}$ are as previously defined). These compounds may be prepared by a Wittig reaction using, for example, $Ph_3P$=$CHR^d$ or $(EtO)_3P(O)$=$CHR^d$. These alkenyl intermediates may be reduced using, for example, catalytic hydrogenation to give compounds wherein $R^7$ is $(CH_2)_pNR^9R^{10}$, $(CH_2)_pCO_2R^{16}$, $(CH_2)_pCONR^9R^{10}$ or $(CH_2)_pNR^9COR^{16}$ and p is 2 to 4.

Compounds wherein $R^7$ is $CONR^9R^{10}$ may be prepared by the reaction of a compound of formula (I) wherein $R^7$ is $CO_2R^{16}$, and $R^{16}$ is methyl, with an amine of the formula $HNR^9R^{10}$ by known methods. Subsequent reduction using, for example, borane in tetrahydrofuran may be used to give a compound wherein $R^7$ is $(CH_2)_pNR^9R^{10}$ in which p is 1. Where one or both of $R^9$ and $R^{10}$ in the resultant amine is a hydrogen atom, the amine may be further converted into a compound wherein $R^7$ is $(CH_2)_pNR^9COR^{16}$ by reaction with, for example, an acyl chloride of the formula $R^{16}COCl$ by known methods.

Compounds wherein $R^7$ is $CH_2OH$ may be prepared by the reduction of a compound of formula (I) wherein $R^7$ is $CO_2R^{16}$, and $R^{16}$ is methyl, using, for example, lithium aluminium hydride. The primary alcohol may be used to prepare a compound of formula (I) wherein $R^7$ is $(CH_2)_pOR^{16}$ and p is 1 by reaction with a halide of the formula $R^{16}Hal$, where Hal is as previously defined in the presence of a suitable base such as sodium hydride.

If a compound of the formula (I) is required in which $R^6$ is an alkyl group it may be prepared via a corresponding compound of the formula (I) in which $R^7$ is $CO_2R^{16}$ group by reaction with KHMDS and an alkyl iodide, followed, if desired, by conversion of the $CO_2R^{16}$ group as described above.

According to a further general process (D), compounds of formula (I) wherein $R^8$ represents H and n is 2 or 3 may be prepared from a compound of formula (VI)

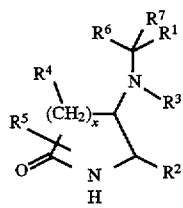

wherein $R^1$, $R^2$, $R^3$, $R^4$, $R^5$, $R^6$, and $R^7$ are as defined for formula (I) and x is 1 or 2 by reduction. Suitable reducing agents will be readily apparent to one skilled in the art and include, for example, borane or metallic hydrides, such as lithium aluminium hydride or sodium borohydride. Borane is preferred.

Compounds of formula (VI) wherein $R^6$ is $C_{1-6}$alkyl and $R^7$ is H may be prepared by reductive amination of a compound of formula (VII)

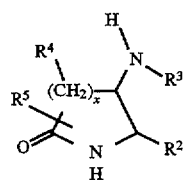

wherein $R^2$, $R^3$, $R^4$, and $R^5$ are as defined for formula (I) except that any reactive moiety is protected by a suitable protecting group and x is 1 or 2, using, for example, sodium cyanoborohydride or sodium triacetoxyborohydride and a compound of the formula $R^1COR^6$ where $R^6$ is $C_{1-6}$alkyl. The reaction is generally effected in a polar solvent such as acetic acid or methanol at a temperature between 0° and 50° C., conveniently at room temperature.

Alternatively, compounds of formula (VI) may be prepared by the reaction of a compound of formula (VII) with a compound of formula (III) in which $R^{31}$ is a leaving group such as a halogen atom, for example, a bromine atom. The reaction is effected in the presence of a base, for example, potassium carbonate and in a suitable solvent such as dimethylformamide.

It will be appreciated that the product of the reductive amination method described herein will be a mixture of stereoisomers at the position of the group $R^6$. For the subsequent preparation of a specific isomer of a compound of formula (I) wherein $R^6$ is $C_{1-6}$alkyl and $R^7$ is H, the mixture of stereoisomers may be resolved by conventional methods, for example, by column chromatography.

Methods for the preparation of intermediates of formula (VII) and formula (II) when $R^{30}$ is $NHR^3$ are described, for example, in European Patent Specification No. 0 436 334.

Where they are not commercially available, the intermediates of formula (III) above may be prepared by the procedures described in the accompanying Examples or by alternative procedures which will be readily apparent to one skilled in the art.

Where the above-described processes for the preparation of the compounds according to the invention give rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, compounds which contain a hydroxy group may be resolved into their component enantiomers by standard techniques, such as the formation of diastereomeric esters or amides, followed by chromatographic separation or separation by fractional crystallization and removal of the chiral auxiliary. Where they are intermediates, diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the NK1 receptor of less than 150 nM.

The compounds of this invention may be formulated as specifically illustrated at pages 35 to 36 of International Patent Specification No. WO 93/01165.

The following Examples illustrate the preparation of compounds according to the invention.

Intermediate 1 cis-5-((3,5-Bis(trifluoromethyl))(α-methyl)benzylamino)-6-(4-fluorophenyl)-2-oxo-piperidine (isomers A and B)

5-Amino-6-(4-fluorophenyl)-2-oxo-piperidine (1.7 g), citric acid (0.8 g) and bis(trifluoromethyl)acetophenone (2.3 g) were dissolved in methanol (30 ml), powdered 4 Å molecular sieves (2 g) were added. After stirring for 5 minutes sodium cyanoborohydride (0.56 g) was added, after stirring for a further 60 minutes the mixture was evaporated to dryness. The residue was suspended in dichloromethane (30 ml) and filtered through celite, the filtrate was then washed with 5% aqueous sodium bicarbonate (20 ml), then dried ($MgSO_4$) and the solvent evaporated. The residue was purified by chromatography on silica (ethyl acetate:methanol, 9:1 ), to afford (isomer A) cis-5-((3,5-bis(trifluoromethyl))(α-methyl)benzylamino)-6-(4-fluorophenyl)-2-oxo-piperidine (0.52 g) mp 138° C., and, (isomer B) cis-5-((3,5-bis(trifluoromethyl))(α-methyl)benzylamino)-6-(4-fluorophenyl)-2-oxo-piperidine (0.21 g) mp 120° C.

Intermediate 2 cis-5-((3,5-Bis(trifluoromethyl))benzylamino)-6-(4-fluorophenyl)-2-oxo-piperidine 5-Amino-6-(4-fluorophenyl)-2-oxo-piperidine (1 g), citric acid (0.5 g) and bis(trifluoromethyl)benzaldehyde (1.3 g) were dissolved in methanol (20 ml), powdered 4 Å molecular sieves (2 g) were added. After stirring for 5 minutes sodium cyanoborohydride (0.34 g) was added, after stirring for a further 60 minutes the mixture was evaporated to dryness. The residue was suspended in dichloromethane (30 ml) and filtered through celite, the filtrate was then washed with 5% aqueous sodium bicarbonate (20 ml), then dried ($MgSO_4$) and the solvent evaporated. The residue was purified by chromatography on silica (ethyl acetate:methanol, 9:1), to afford cis-5-((3,5-bis(trifluoromethyl))benzylamino)-6-(4-fluorophenyl)-2-oxo-piperidine (1.1 g)

$^1H$ NMR 1.64–1.72 (1H,m), 2.13–2.49 (3H,m), 2.95 (1H,br s), 377–3.86 (2H,m), 4.66 (1H,br s), 7.14 (2H,t,J=6 Hz), 7.28(2H,t,J=6 Hz), 7.76 (1H,s), 7.82 (2H,s), 7.88 (1H,s).

Intermediate 3 cis-3-((3,5-Bis(trifluoromethyl))benzylamino)-2-(4-fluorophenyl)piperidine cis-5-((3,5-Bis(trifluoromethyl))benzylamino)-6-(4-fluorophenyl)-2-oxo-piperidine (1 g) was dissolved in tetrahydrofuran (15 ml), a solution of borane in THF was added dropwise (4.4 ml of 1M solution), the resulting solution was then heated at reflux for 2 hours. The mixture was then cooled to room temperature and methanol (5 ml) added dropwise, the resulting mixture was evaporated to dryness. The residue was dissolved in ethanol (20 ml) potassium carbonate (1 g) added and the mixture heated at reflux for 4 hours. The mixture was then evaporated to dryness and the residue extracted with hot dichloromethane (2×20 ml), ethereal HCl was added to the extracts and the product isolated by filtration. Recrystallisation from ethanol/ether afforded cis-3-((3,5-bis(trifluoromethyl))benzylamino)-2-(4-fluorophenyl)piperidine as a dihydrochloride salt m.p. 290° C.

EXAMPLE 1 cis-3-((3,5-Bis(trifluoromethyl)(α-methyl)benzylamino)-2-(4-fluorophenyl)piperidine (Isomer B)

Cis-5-((3,5-Bis(trifluoromethyl))(α-methyl) benzylamino)6-(4-fluorophenyl)-2-oxo-piperidine (isomer B) (0.2 g) was dissolved in tetrahydrofuran (15 ml), a solution of borane in THF was added dropwise (2 ml of 1M soln), the resulting solution was then heated at reflux for 2 hours. The mixture was then cooled to room temperature and methanol (5 ml) added dropwise, the resulting mixture was evaporated to dryness. The residue was dissolved in ethanol (20 ml) potassium carbonate (1 g) added and the mixture heated at reflux for 4 hours. The mixture was then evaporated to dryness and the residue extracted with hot dichloromethane (2×20 ml), ethereal HCl was added to the extracts and the product isolated by filtration. Recrystallisation from ethanol/ether afforded cis-3-((3,5-bis(trifluoromethyl))(α-methyl)benzylamino)-2-(4-fluorophenyl)piperidine (Isomer B) as a dihydrochloride salt. m.p. 235° C.

EXAMPLE 2 cis-5-[3-((3,5-Bis(trifluoromethyl))benzylamino)-2-(4-fluorophenyl)piperidin-1-ylmethyl]-2,4-dihydro-[1,2,4]-triazol-3-one cis-3-((3,5-Bis(trifluoromethyl))benzylamino)-2-(4-fluorophenyl)piperidine dihydrochloride salt (0.68 g) was partitioned between chloroform (50 ml) and 10% aqueous potassium bicarbonate (20 ml), the organic phase was separated, dried ($Na_2SO_4$) and evaporated to afford the free base (0.5 g). The free base was dissolved in DMF (19 ml) and $K_2CO_3$ (0.8 g), N-carbomethoxy-2-chloroacetamidrazone (0.2 g) was added and the mixture heated to 60° C. for 30 minutes. The mixture was then heated to 140° C. for a further 2 hours, cooled to room temperature and the solvent removed at reduced pressure. The residue was purified by chromatography (ethyl acetate:methanol, 9:1), the oil isolated was dissolved in dichloromethane and treated with ethereal HCl to afford the dihydrochloride salt, mp 225° C.

EXAMPLE 3 cis-(±)-3-(2-Hydroxy-1-(4-fluorophenyl)ethylamino)-2-phenylpiperidine a) To a methanol (5 ml) solution of (±) 5-amino-6-phenylpiperidin-2-one (1.67 g, cis:trans isomers (6:1)) was added a solution of toluene-4-sulphonic acid monohydrate (1.8 g) in methanol (5 ml). The solid which formed by crystallization was removed by filtration to give pure cis isomer; mp 242°–244° C. A sample of this material (0.9 g) was dissolved in warm water (10 ml) and this solution was applied to a column containing Dowex™ 50W-X8 ($H^+$form, 20 ml). After washing the column with water the product was eluted with dilute aqueous ammonia (2M) and the fractions containing product were evaporated to dryness. To a solution of the residue (0.32 g) in dimethylformamide (5 ml) was added $K_2CO_3$ (0.7 g) and 2-bromo-2-(4-fluorophenyl)acetic acid (0.42 g). After stirring at room temperature for 16h, water (20 ml) and ethyl acetate (20 ml) were added and the organic phase washed with water, saturated in brine and dried ($MgSO_4$). The solvent was removed in vacuo and the residue purified on silica gel eluting with ethyl acetate to give, as a 0.7:1 mixture of diastereomers, methyl cis(±)5-(N-(4-fluorophenylglycinate))-6-phenylpiperidin-2-one. $^1$H NMR (250 MHz, $CDCl_3$) δ7.45–7.09 (9H,m), 5.97 (0.4H,br d), 5.77 (br s), 4.90 (m), 4.78 (d, J=3.6 Hz), 4.68 (d, J=3.5 Hz), 4.6 (m), 4.05 (s+s), 3.61 (s, OMe), 3.54 (s, OMe), 3.08 (m), 2.87 (m), 2.75–2.3 (m), 1.90 (m). MS m/z ($CI^+$) 357 (M+H).

b) A solution of the diastereomeric mixture (Example 3a, 0.32 g) in tetrahydrofuran (4 ml) was added to a solution of lithium aluminium hydride (1M in tetrahydrofuran, 2 ml). The solution was stirred at room temperature for 15 minutes then at 40° C. for 1 hour. Water (20 ml) was added carefully to the solution followed by ethyl acetate (20 ml). The organic phase was washed with saturated brine and dried ($MgSO_4$). The residue after evaporation was chromatographed on silica gel eluting with a gradient between $CH_2Cl_2$ and methanol, $CH_2Cl_2$, aqueous ammonia (10:90:0.4) to give after crystallization from diethylether:

diastereomer A: mp=157°–159° C., $^1$H NMR (250 MHz, $CDCl_3$) δ7.33–7.18 (5H, m, phenyl), 6.7 (dd, 2H, J=8.72 Hz), 6.51 (2H, dd, J=8.64 Hz, 5.44 Hz, aryl), 3.89 (1H, d, J=2.4 Hz, NHCHPh), 3.5 (2H, m), 3.22 (2H, m), 3.00 (1H, vbr s), 2.80 (1H, td, J=12.01, 2.75 Hz), 2.70 (1H, d, J=2.49 Hz), 1.90 (2H, m), 1.54 (2H, m) m/z ($CI^+$) 315 (M+H); and diastereomer B: mp=116°–120° C., $^1$H NMR (250 MHz, $CDCl_3$) δ7.38–7.25 (5H, m), 7.0 (2H, dd, J=6.6, 8.7 Hz), 6.74 (2H, dd, J=8.7, 8.7 Hz), 3.8 (1H, d, J=2.3 Hz), 3.28 (1H, dd, J=10.6, 4.5 Hz), 3.18 (2H, m), 3.04 (1H, m), 2.78 (2H, m), 1.60 (3H, m), 1.37 (1H, m) m/z ($CI^+$) 315 (M+H).

EXAMPLE 4 cis-(±)-3-(2-Hydroxy-1-phenylethylamino)-phenylpiperidine

The title compound was prepared in an analogous manner to that described in Example 3 using (±) 5-amino-6-phenylpiperidin-2-one and 2-bromo-2-phenylacetic acid as starting materials. MS m/z ($CI^+$) 297 (M+H).

We claim:

1. A compound of formula (I), or a pharmaceutically acceptable salt:

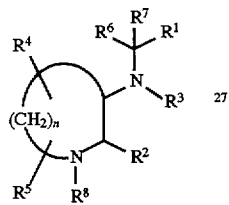
(I)

wherein n is 1, 2 or 3 and where any carbon atom of $(CH_2)_n$ may be substituted by $R^4$ and/or $R^5$;

$R^1$ represents $(CH_2)_q$phenyl, wherein q is zero, 1, 2 or 3, which may be optionally substituted in the phenyl ring by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ and —$CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^3$ represents H or $C_{1-6}$alkyl;

$R^4$ and $R^5$ each independently represent H, halo, $C_{1-6}$alkyl, oxo, $CO_2R^a$ or $CONR^aR^b$;

$R^6$ represents H or $C_{1-6}$alkyl;

$R^7$ represents H, $C_{1-6}$alkyl optionally substituted by a hydroxy group, or $(CH_2)_pNR^9R^{10}$, $CO_2R^{16}$, $CONR^9R^{10}$, $(CH_2)_pCO_2R^{16}$, $(CH_2)_pCONR^9R^{10}$, $(CH_2)_pNR^9COR^{16}$, $(CH_2)_pNHSO_2R^{11}$, $(CH_2)_pOR^{16}$, $(CH_2)_pOC(O)R^9$, $(CH_2)_pOC_{1-4}$alkylCOR$^{17}$, or phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ and —$CONR^aR^b$;

$R^8$ represents $C_{1-6}$alkyl, optionally substituted by oxo, substituted by an optionally substituted aromatic heterocycle.

with the proviso that when $R^6$ and $R^7$ both represent H, $R^8$ represents $C_{1-6}$alkyl optionally substituted by oxo, substituted by an optionally substituted aromatic heterocycle selected from pyrrolyl, pyrazolyl, pyrazinyl, pyridazinyl, oxadiazolyl, thiadiazolyl, imidazolyl, benzimidazolyl, benzoxazolyl, benzthiophenyl, benzofuranyl and indolyl, or a substituted aromatic heterocycle selected from thienyl, furyl, pyridyl, triazolyl, tetrazolyl, thiazolyl, oxazolyl, quinolyl, isoxazolyl and isothiazolyl;

$R^a$ and $R^b$ each independently represent H, $C_{1-6}$alkyl, trifluoromethyl or phenyl optionally substituted by $C_{1-6}$alkyl, halo or trifluoromethyl;

$R^9$ and $R^{10}$ each independently represent H or $C_{1-6}$alkyl;

$R^{11}$ represents $NR^{14}R^{15}$ or an optionally substituted aromatic or non-aromatic azacyclic or azabicyclic group;

$R^{12}$ represents $OR^a$, $CONR^aR^b$ or heteroaryl;

$R^{13}$ represents H or $C_{1-6}$alkyl;

$R^{14}$ and $R^{15}$ each independently represent H, $C_{1-6}$alkyl, phenyl optionally substituted by one or more of $C_{1-6}$alkyl, $C_{1-6}$alkoxy, halo or trifluoromethyl, or phenyl$C_{1-4}$alkyl optionally substituted in the phenyl ring by one or more of $C_{1-6}$alkyl, $C_{1-6}$alkoxy, halo or trifluoromethyl;

$R^{16}$ represents $C_{1-6}$alkyl;

$R^{17}$ represents $C_{1-6}$alkoxy, amino, $C_{1-4}$alkylamino or di($C_{1-4}$alkyl)amino; and p is 1 to 4.

2. A compound as claimed in claim 1 of formula (Ia), or a pharmaceutically acceptable salt thereof:

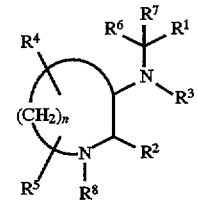
(Ia)

wherein $R^1$, $R^2$, $R^3$, $R^4$, $R^5$, $R^6$, $R^8$ and n are as defined in claim 1; and $R^7$ represents $C_{1-6}$alkyl optionally substituted by a hydroxy group, or $(CH_2)_pNR^9R^{10}$, $CO_2R^{16}$, $CONR^9R^{10}$, $(CH_2)_pCO_2R^{16}$, $(CH_2)_pCONR^9R^{10}$, $(CH_2)_pNR^9COR^{16}$, $(CH_2)_pNHSO_2R^{11}$, $(CH_2)_pOR^{16}$, $(CH_2)_pOC(O)R^9$, $(CH_2)_pOC_{1-4}$alkylCOR$^{17}$, or phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ and —$CONR^aR^b$.

3. A compound as claimed in claim 1 of formula (Ib), or a pharmaceutically acceptable salt thereof:

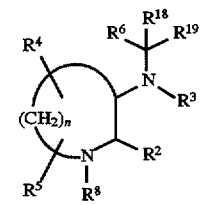
(Ib)

wherein $R^2$, $R^3$, $R^4$, $R^5$, $R^6$, $R^8$ and n are as defined in claim 1;

$R^{18}$ represents $C_{1-6}$alkyl optionally substituted by a hydroxy group; and $R^{19}$ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ and —$CONR^aR^b$.

4. A compound as claimed in claim 1 of formula (Ic), or a pharmaceutically acceptable salt thereof:

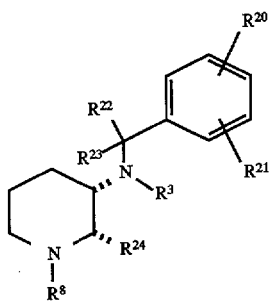

wherein

R³ and R⁸ are as defined in claim 1;

R²⁰ and R²¹ independently represent H, $C_{1-6}$alkyl, $C_{2-6}$alkenyl, $C_{2-6}$alkynyl, chloro, bromo, fluoro, iodo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ are as previously defined;

R²² is methyl optionally substituted by hydroxy;

R²³ is H or methyl; and

R²⁴ represents phenyl or benzhydryl wherein any of the phenyl rings of the phenyl or benzhydryl moieties may optionally be substituted by halo or trifluoromethyl.

5. A compound as claimed in claim 1 of formula (Id), or a pharmaceutically acceptable salt thereof:

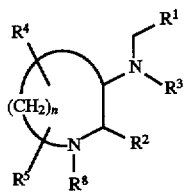

wherein

R¹, R², R³, R⁴, R⁵, and n are as defined in claim 1; and

R⁸ represents $C_{1-6}$alkyl, optionally substituted by oxo, substituted by an optionally substituted aromatic heterocycle selected from pyrrolyl, pyrazolyl, pyrazinyl, pyridazinyl, oxadiazolyl, thiadiazolyl, imidazolyl, benzimidazolyl, benzoxazolyl, benzthiophenyl, benzofuranyl and indolyl, or a substituted aromatic heterocycle selected from thienyl, furyl, pyridyl, triazolyl, tetrazolyl, thiazolyl, oxazolyl, quinolyl, isoxazolyl and isothiazolyl.

6. A compound as claimed in claim 1 of formula (Ie), or a pharmaceutically acceptable salt thereof:

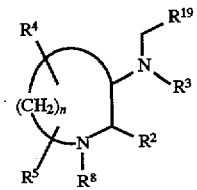

wherein R², R³, R⁴, R⁵, R⁸ and n are as defined in claim 1; and

R¹⁹ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, $-OR^a$, $-SR^a$, $-SOR^a$, $-SO_2R^a$, $-NR^aR^b$, $-NR^aCOR^b$, $-NR^aCO_2R^b$, $-COR^a$, $-CO_2R^a$ and $-CONR^aR^b$.

7. A compound as claimed in claim 1 of formula (If), or a pharmaceutically acceptable salt thereof:

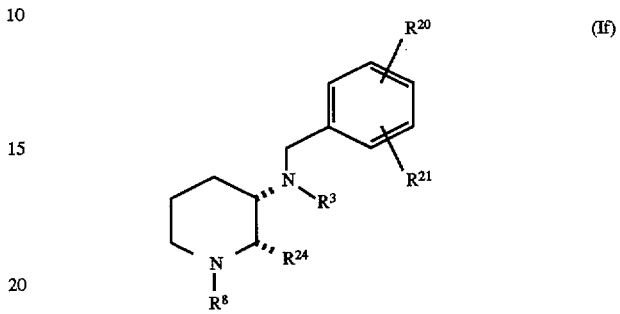

wherein

R³ and R⁸ are as defined in claim 1;

R²⁰ and R²¹ independently represent H, $C_{1-6}$alkyl, $C_{2-6}$alkenyl, $C_{2-6}$alkynyl, chloro, bromo, fluoro, iodo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ are as previously defined; and R²⁴ represents phenyl or benzhydryl wherein any of the phenyl rings of the phenyl or benzhydryl moieties may optionally be substituted by halo or trifluoromethyl.

8. A compound which is cis-[3-((3,5-bis(trifluoromethyl))benzylamino)-2-(4-fluorophenyl)piperidine-1-ylmethyl]-2,4-dihydro-[1,2,4]-triazol-3-one; or a pharmaceutically acceptable salt thereof.

9. A pharmaceutical composition comprising a compound as claimed in claim 1 in association with a pharmaceutically acceptable carrier or excipient.

10. A method for the treatment or prevention of physiological disorders associated with an excess of tachykinins, which method comprises administration to a patient in need thereof of a tachykinin reducing amount of a compound according to claim 1, or a pharmaceutically acceptable salt thereof.

11. A method according to claim 10 for the treatment or prevention of pain or inflammation.

12. A method according to claim 10 for the treatment or prevention of migraine.

13. A method according to claim 10 for the treatment or prevention of emesis.

* * * * *